(12) United States Patent
Toppo

(10) Patent No.: US 6,403,658 B1
(45) Date of Patent: Jun. 11, 2002

(54) GENITAL VASODILATOR

(76) Inventor: Shaina Toppo, 3080 Yankee Clipper Dr., Las Vegas, NV (US) 89117

( * ) Notice: Subject to any disclaimer, the term of this patent is extended or adjusted under 35 U.S.C. 154(b) by 0 days.

(21) Appl. No.: 09/666,278

(22) Filed: Sep. 21, 2000

(51) Int. Cl.⁷ ................ A61P 15/10; A61K 31/4406; A61K 31/352; A61K 31/7032; A61M 37/00
(52) U.S. Cl. ............ 514/929; 514/25; 514/456; 514/356; 424/449
(58) Field of Search .................. 514/310, 356, 514/929, 969, 783, 182, 25, 456; 424/195.1, 449

(56) References Cited

U.S. PATENT DOCUMENTS 3,864,362 A * 2/1975 Feuer et al. ............ 260/345.2
5,523,087 A * 6/1996 Shlyankevich ............ 424/195.1

* cited by examiner

*Primary Examiner*—Edward J. Webman
*Assistant Examiner*—Helen Nguyen

(57) ABSTRACT

The goal in the treatment of female dysfunction is to increase blood flow to the genitals. Heretofore, treatments/developments have focused on prostaglandin E-I creams, topical sildenafil, aminoacids, etc, ingested systemic medications such as sildenafil, phentolamine, etc and mechanical devices. Our invention is a direct, local topical vasodilator with plant estrogen added to eliminate genital dryness, N-methylnicotinate and DHEA which is precusor for, among others, the hormone testosterone. Testosterone is important in both male and female sexuality.

6 Claims, No Drawings

GENITAL VASODILATOR

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not applicable

BACKGROUND OF THE INVENTION

Recent scientific publications (e.g.. The Journal of the American Medical Associations) have reported that 43% of women experience some kind of sexual dysfunction. Some investigators have assigned four subclasses to the general term of female sexual dysfunction: 1) Sexual Arousal Disorder—whereby sexual thoughts occur, however, these thoughts are not communicated to the clitoris, 2) Orgasmic Disorder—inability to have orgasm, 3) Sexual Pain Disorder—involuntary vaginal muscle spasm which prohibits penile penetration and 4) Hypoactive Sexual Desire—patient lacks libido and sexual thoughts.

BRIEF SUMMARY OF THE INVENTION

N-methylnicotinate is a very potent vasodilator. When applied to the clitoris during stimulation, the clitoris becomes red, increases in size and has a "prickly" sensation. Women who previously have suffered from sexual dysfunction, report orgasms. Also, women who have had normal orgasms have reported increases in both the intensity and number of orgasms.

The clitoris, which means "key" in the Greek language is the most important part of a woman's sexual anatomy. In order for a woman to have an orgasm, the corpora cavernous which is located within the clitoris, must become engorged with blood and enlarge.

Many women have complained of genital dryness. Therefore, we have added plant extract estrogen which alleviates this problem.

DHEA is a precusor for Testosterone which is necessary for both male and female sexual function.

BRIEF DESCRIPTION OF THE SEVERAL VIEWS OF THE DRAWING

Not Applicable.

Three of these conditions (#'s 1, 2 and 3) may be treated successfully by increasing blood flow to the clitoris during stimulation.

DETAILED DESCRIPTION OF THE INVENTION

The active ingredient is N-methylnicotinate and its derivatives at a potency up to and including 4% plus varying amounts of plant estrogen and DHEA set in a cream/emolient base in a transdermal patch system.

What is claimed is:

1. A composition for treating female sexual dysfunction comprising up to 4% N-methylnicotinate and an amount of plant extract estrogen effective for alleviating genital dryness.
2. The composition of claim 1 is in the form of a cream.
3. The composition of claim 1 further comprising an emollient.
4. The composition of claim 2 contained in a transdermal patch.
5. The composition of claim 3 contained in a transdermal patch.
6. A method of treatment of female sexual dysfunction comprising the topical application of the composition according to claims 1 to 4.

* * * * *